(12) United States Patent
Weis et al.

(10) Patent No.: US 8,394,338 B2
(45) Date of Patent: Mar. 12, 2013

(54) PROCESS FOR HYDROPHILIZING SURFACES OF FLUIDIC COMPONENTS AND SYSTEMS

(75) Inventors: Léonie Weis, Graz (AT); Dietmar Werkl, Graz (AT); Marco Leiner, Graz (AT); Werner Ziegler, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 949 days.

(21) Appl. No.: 11/106,143

(22) Filed: Apr. 14, 2005

(65) Prior Publication Data

US 2005/0255579 A1    Nov. 17, 2005

(30) Foreign Application Priority Data

Apr. 26, 2004  (EP) .................................. 04009817

(51) Int. Cl.
*B01L 3/00*    (2006.01)
(52) U.S. Cl. .............. 422/500; 422/83; 422/98; 436/68; 436/137
(58) Field of Classification Search ........................ None
See application file for complete search history.

(56) References Cited

U.S. PATENT DOCUMENTS

| | | | |
|---|---|---|---|
| 3,874,850 A | 4/1975 | Sorensen et al. | |
| 4,269,685 A | 5/1981 | Parker | |
| 4,534,355 A | 8/1985 | Potter | |
| 4,734,445 A | 3/1988 | Noda et al. | |
| 4,752,426 A | 6/1988 | Cho | |
| 4,835,211 A | 5/1989 | Noda et al. | |
| 4,880,883 A | 11/1989 | Grasel et al. | |
| 4,885,077 A | 12/1989 | Karakelle et al. | |
| 5,212,000 A | 5/1993 | Rose et al. | |
| 5,322,063 A | 6/1994 | Allen et al. | |
| 5,728,762 A | 3/1998 | Reich et al. | |

(Continued)

FOREIGN PATENT DOCUMENTS

EP    0 379 156 A2    7/1990
EP    0 483 941 A2    3/1991

(Continued)

OTHER PUBLICATIONS

Moritani, T. et al. DNA capillary electrophoresis using poly(vinyl alcohol. I. Inner capillary coating, 2003, Elecrtophoresis, vol. 24, pp. 2764-2771.*

(Continued)

*Primary Examiner* — Robert Xu
(74) *Attorney, Agent, or Firm* — McDonnell Boehnen Hulbert & Berghoff LLP

(57) ABSTRACT

A process for producing a film of a hydrophilic polymer on the inner surfaces of a fluidic component is provided comprising subjecting the inner surfaces of the fluidic component to a physicochemical pre-treatment, contacting the inner surfaces of the fluidic component with a solution of the hydrophilic polymer, replacing the solution of the hydrophilic polymer with a gaseous medium in such a manner that firstly the inner surfaces of the fluidic component remain wetted with part of the polymer solution, and removing the solvent to produce a film of the hydrophilic polymer on the inner surfaces of the fluidic component. The hydrophilic polymer used has a surface wettability for aqueous solutions which is higher than the surface wettability of the inner surfaces of the fluidic component itself.

22 Claims, 2 Drawing Sheets

U.S. PATENT DOCUMENTS

| | | | |
|---|---|---|---|
| 5,860,676 A * | 1/1999 | Brzezicki et al. | 285/24 |
| 5,932,200 A | 8/1999 | Reich et al. | |
| 6,001,067 A | 12/1999 | Shults et al. | |
| 6,080,583 A | 6/2000 | Von Bahr | |
| 6,370,941 B2 | 4/2002 | Nakamura et al. | |
| 6,432,510 B1 | 8/2002 | Kim et al. | |
| 6,444,324 B1 * | 9/2002 | Yang et al. | 428/447 |
| 6,447,835 B1 | 9/2002 | Wang et al. | |
| 6,509,148 B2 | 1/2003 | Cha et al. | |
| 6,586,038 B1 | 7/2003 | Chabrecek et al. | |
| 6,893,547 B2 | 5/2005 | Gascoyne et al. | |
| 6,939,450 B2 | 9/2005 | Karinka et al. | |
| 8,187,543 B2 | 5/2012 | Weis | |
| 2004/0062854 A1 | 4/2004 | Jan et al. | |
| 2005/0054774 A1 * | 3/2005 | Kangas | 525/123 |
| 2005/0055044 A1 | 3/2005 | Kangas | |
| 2005/0249885 A1 | 11/2005 | Weis et al. | |

FOREIGN PATENT DOCUMENTS

| | | |
|---|---|---|
| EP | 1 106 363 B1 | 6/2001 |
| JP | 2000-202907 A | 7/2000 |
| WO | WO 94/06485 | 3/1994 |
| WO | 97/17607 | 5/1997 |
| WO | 01/33195 | 5/2001 |
| WO | WO 02/070590 A2 | 9/2002 |
| WO | WO 02/085185 * | 10/2002 |
| WO | WO 03/072158 A1 | 9/2003 |
| WO | 03/087783 | 10/2003 |

OTHER PUBLICATIONS

Kim, S.R., "Surface Modification of Poly(tetrafluoroethylene) Film by Chemical Etching, Plasma, and Ion Beam Treatments", Journal of Applied Polymer Science, vol. 77, 1913-1920 (2000).

Linek et al., "Measurement of Oxygen by Membrane—Covered Probes: Guidelines for Applications in Chemical and Biochemical Engineering," Ellis Horwood Limited, (1988) section 5.3, part of section 5.4 and figure 5.1.

Noda Isao: "Plastic and rubbers with water-wettable surfaces," Chemistry and Industry, Oct. 21, 1991, http://www.highbeam.com/doc/1G1-11547105.html, 2 pages.

Ulubayram, Kezban et al.: "Properties of plasma-modified polyurethane surfaces," Colloids and Surfaces B. Biointerfaces, vol. 1, Issue 4, Sep. 23, 261-269.

Wan, Yuqing, et al.: "Biodegradable poly(l-lactide)-poly(ethylene glycol) multiblock copolymer: synthesis and evaluation of cell affinity," Center for Molecular Sciences, Institute of Chemistry, Chinese Academy of Sciens, Beijing 100080, china, received Oct. 29, 2002, accepted Dec. 9, 2002, Biomaterials 24 (2003), pp. 2195-2203.

Li, Xu et al.: "Poly(ester urethane)s Consisting of Poly[(R)-3-hydroxybutyrate] and Poly(ethylene glycol) as Candidate Biomaterials: Characterization and mechanical Property Study," Biomacromolecules, 2005 6(5), pp. 274-2747.

Bertozzi, Carolyn R.: "Development and testing of new biologically-based polymers as advanced biocompatible contact lenses," Lawrence Berkeley National Laboratory, http://escholarship.org/uc/item/799564wq, Jun. 1, 2000 (7 pages).

* cited by examiner

PROCESS FOR HYDROPHILIZING SURFACES OF FLUIDIC COMPONENTS AND SYSTEMS

CROSS-REFERENCE TO RELATED APPLICATION

This application claims priority to European Patent Application No. 04 009 817.0 filed Apr. 26, 2004, the disclosure of which is incorporated herein by reference.

BACKGROUND OF THE INVENTION

The present invention is directed to processes for hydrophilizing surfaces of fluidic components and systems.

Modern analytical systems for determining physical or chemical parameters of a liquid often have complex fluidic systems which have to ensure that the liquid to be examined is transported substantially without interference and carry-over to the sensory elements and that the liquid sample is transported away from the sensory elements after determining the parameters.

Such analytical systems are used in particular in clinical diagnostics where they are used especially for blood gas analysis or for other measurements of samples present in a liquid form. Such systems are used for example to determine the oxygen or carbon dioxide partial pressure of blood, haemoglobin parameters such as total haemoglobin, oxyhaemoglobin, carboxyhaemoglobin or methaemoglobin of whole blood or haemolysed blood, the haematocrit value of whole blood as well as the pH value or the concentration of ions such as lithium, sodium, potassium, magnesium, calcium or chloride or special metabolites such as glucose, urea, creatinine or lactate in physiological liquids. Such complex analytical systems often have different sensory elements to determine the respective parameters which are used for many determinations. Such sensory elements are for example electrochemical or optical sensors for determining the gas values, the pH value, the ion values and the metabolite values or the optical measuring devices for determining the haemoglobin values.

In addition to such systems, systems are also known which can be used in the direct vicinity of the patient and in which the liquid sample is transferred directly from the patient into the analytical system by means of a tube system.

In addition to fluidic partial systems for transporting the sample liquid and/or quality control media, many analytical systems often also contain other fluidic partial systems in order to, for example, transport liquid or even gaseous calibration media and/or wash or cleaning media from storage containers to the sensory elements and from there to waste containers. The transport of the various media is controlled by pumps and valves along paths that differ in parts.

Such modern instruments often use very small amounts of sample and liquid that are often aliquoted again in the fluidic system. Depending on the number and type of parameters to be determined, the required sample volume can for example be between about 50 and about 120 microliters. However, special measures are required to ensure that such small sample volumes are transported without contamination to the sensory elements of the analytical system. Contamination can for example be caused by residues of the previous samples or of control, calibration, or cleaning media remaining in the fluidic system. In order to avoid such contamination, washing and drying steps can for example be inserted between the individual determinations of the measured values.

In the case of sensory elements for determining gases such as electrochemical or optical gas sensors, but also in the case of optical measuring systems for example to determine haemoglobin, there is still a risk that measurement errors occur due to the inclusion of gas bubbles in the fluidic system, especially in the area of the sensory elements. Thus when gaseous analytes are determined in liquids by means of electrochemical gas sensors, problems can occur in the sample measurement or in the calibration or quality control when the sample or the quality control or calibration agent does not completely fill the liquid-conveying area of the sensory element or when there are gas bubbles such as air bubbles in this area. Gas bubbles form especially when non-uniform inner surfaces are present within the fluidic system which have different wetting properties for liquids. Gas bubbles are formed or become attached especially frequently at sites in the fluidic system at which there is a sudden transition in the wetting properties of the inner surfaces of the various fluidic components. This is, for example, the case when surfaces made of different materials abut one another. However, the fluidic systems of many analytical systems consist of many individual fluidic components made of different materials which have abutting surfaces with different wetting properties. Furthermore, many of the fluidic components of such analytical systems are made of plastics which are characterized by a low hydrophilicity and a hydrophobicity. Such plastic surfaces are poorly wetted with aqueous liquids and have a particular tendency to form or attach gas bubbles.

SUMMARY OF THE INVENTION

It is against the above background that the present invention provides certain unobvious advantages and advancements over the prior art. In particular, the inventors have recognized a need for improvements in processes for hydrophilizing surfaces of fluidic components and systems.

Although the present invention is not limited to specific advantages or functionality, it is noted that the present invention provides processes for improving the surface wettability of the inner surfaces of fluidic components. In particular, the present invention provides a process that can be carried out in the simplest and most economical manner and enables a hydrophilization of the inner surfaces of fluidic components which is stable over a long period of use and is resistant to physical or chemical stress. Further, the present invention provides fluidic components and systems in which the risk of attachment or formation of gas bubbles on the inner surfaces of these fluidic components can be reduced over a long period of use. In addition, the present invention provides analytical systems for determining at least one physical or chemical parameter of a liquid in which the risk of a contamination of the sample liquid especially by the attachment or formation of gas bubbles or other substances on the inner surfaces of these fluidic components can be reduced over a long period of use.

In accordance with one embodiment of the present invention, process for producing a film of a hydrophilic polymer on the inner surfaces of a fluidic component is provided, comprising (a) subjecting the inner surfaces of the fluidic component to a physicochemical pre-treatment, (b) contacting the inner surfaces of the fluidic component with a solution of the hydrophilic polymer, (c) replacing the solution of the hydrophilic polymer with a gaseous medium in such a manner that firstly the inner surfaces of the fluidic component remain wetted with part of the solution of the hydrophilic polymer, and (d) removing the solvent to produce a film of the hydrophilic polymer on the inner surfaces of the fluidic component. In accordance with the present embodiment, the hydrophilic polymer has a surface wettability for aqueous solutions which is higher than the surface wettability of the inner surfaces of the fluidic component in the absence of a film of the hydrophilic polymer.

In accordance with another embodiment of the present invention, a fluidic component comprising a film of a hydrophilic polymer on the inner surfaces of the fluidic component is provided, wherein the film of the hydrophilic polymer is produced using the aforementioned processes according to the present invention. The film of the hydrophilic polymer can be directly present on the inner surfaces of the fluidic component without further intermediate layers.

In accordance with still another embodiment of the present invention, a fluidic system for transporting liquids is provided comprising one or more fluidic components, wherein at least one fluidic component is the fluidic component of the present invention. In accordance with the instant embodiment, the fluidic components can be in fluid communication, such that liquids can be transported there between.

In accordance with yet another embodiment of the present invention, a process for producing a fluidic system in accordance with the present invention is provided comprising producing the film of the hydrophilic polymer on the inner surfaces of individual fluidic components or in smaller subassemblies of such fluidic components, which are subsequently assembled to form the fluidic system.

In accordance with yet still another embodiment of the present invention, a process for producing a fluidic system in accordance with the present invention is provided comprising subjecting the inner surfaces of individual fluidic components or smaller subassemblies of such fluidic components to a physicochemical pre-treatment, assembling the individual fluidic components or smaller subassemblies of such fluidic components to form the fluidic system, and performing process steps b) to d) on the assembled fluidic system, as described herein.

In accordance with yet still another embodiment of the present invention, an analytical system is provided for determining at least one physical or chemical parameter of a liquid comprising at least one sensory element for determining at least one physical or chemical parameter of the liquid, and a fluidic system for transporting liquids to the sensory element and/or from the sensory element, wherein the fluidic system comprises one or more fluidic components on the inner surfaces of which a film of a hydrophilic polymer is present, said film having been produced in accordance with the present invention.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
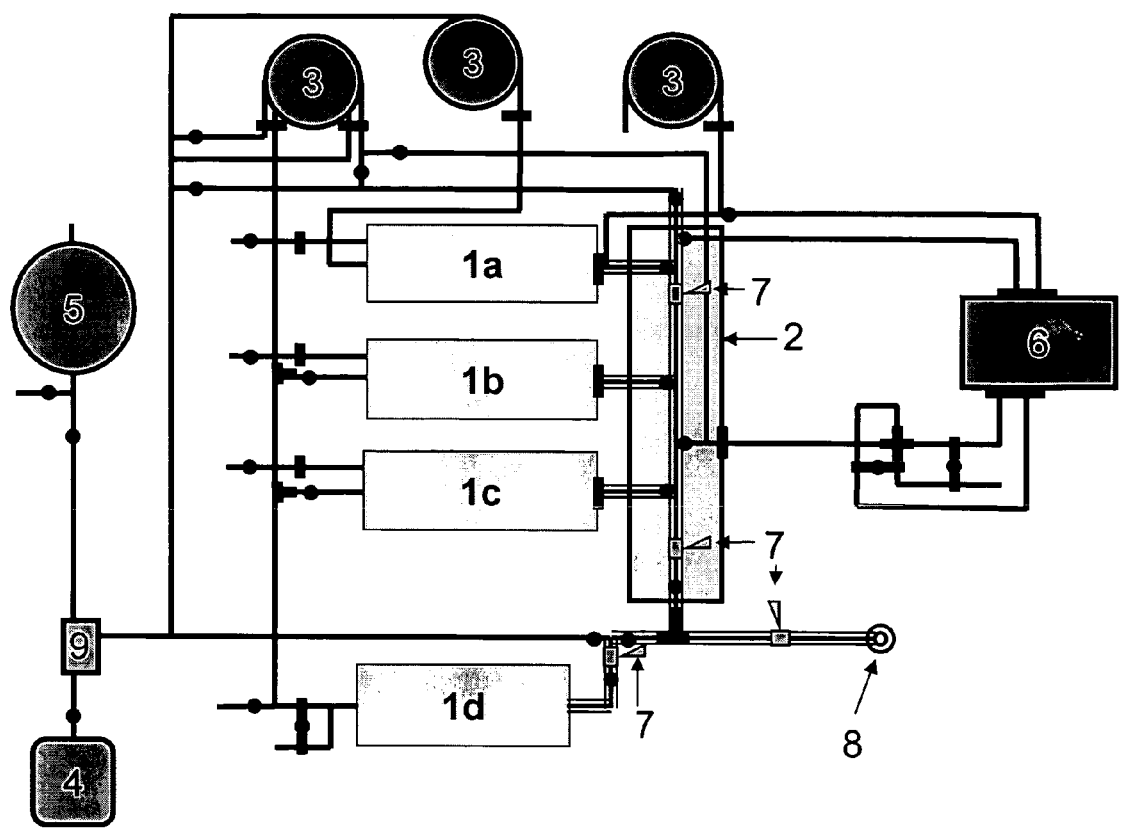
FIG. 1 is a schematic illustration of a fluidic system in accordance with one embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

A fluidic component is basically regarded in the sense of the present application as any component which is suitable for taking up, conveying or dispensing liquids. In particular, components are regarded as fluidic components in the sense of the present invention which, due to their spatial structure, are designed to take up, convey or dispense liquids in a specific and defined manner. Fluidic components are often used as components of a fluidic system and in this connection are used to transport liquids within this system.

Such fluidic components can fulfil various functions and in particular they can be used as liquid containers such as, for example, bottles, reagent packs, separators or waste containers; to transport liquids such as, for example, tubes, pipes, channels or areas of sensory elements that convey liquids; as valves or control elements such as, for example, pinch tube valves, mixing valves, pressure valves or valve T-pieces; as liquid uptake devices such as, for example, needles, tubes or specially formed filling openings; for coupling to various components such as, for example, nipples, dock elastomers, T- or Y-pieces, crossing pieces, angle connectors or plug connectors; or for sealing functions such as, for example, sealing elements. In order to fulfil their function, tubes for example can consist of elastic materials and can typically be used for the defined transport of liquids, for example using pinch valves for regulation. In particular, they can be used in analytical systems for the specific transport of sample liquids to the sensory elements and as components that can be simply assembled to transport liquids away, for example, into a waste container. In contrast, rigid pipes are often manufactured from materials having certain physical properties such as transparency, gas impermeability, thermal conductivity or the ability to be cleaned, and can often be used as fluidic components for liquid transport for areas which do not have to be regulated by pinch valves.

Coupling elements such as plug-in nipples, T- or Y-pieces, crossing pieces, angle connectors or plug-in connectors are often used as fluidic components to make junctions between other fluidic components such as tubes, pipes or also liquid-conveying areas of sensory elements, inter alia. Dock elastomers are embodiments of coupling systems that allow individual components of the fluidic system to be frequently plugged-in or disconnected in a user-friendly manner. Such coupling systems can for example be used for reagent packs in order to couple them to the fluidic system in one operation. Such coupling systems can be used to easily remove and replace individual components of the fluidic system. A particular form of liquid uptake devices are so-called filling mouths. These are used to receive external liquid containers such as capillaries, syringes or adaptors. Such a filling mouth can be used to make a tight fluidic connection between an external sample vessel and a diagnostic analytical system such that in this manner sample liquid can be safely injected or aspirated into the analytical system.

Liquid containers such as bottles or reagent packs can be used to store and provide liquids such as calibration liquids and cleaning and conditioning solutions. The solutions can for example be removed from these liquid containers by suction. Sealing elements are typically used for fluidic coupling for junctions between two non-elastic fluidic components.

Fluidic components can also have more complex devices for transporting liquids such as channel systems. In the sense of the present application, fluidic components can also comprise the liquid-conveying areas of sensory elements. These are understood as the areas of sensory elements which can be in direct contact with the liquid to be examined and thus have inner surfaces in the sense of the present application. This can, for example, be the liquid supply and discharge sample channel within the sensory element or also parts of the sensor itself which come into direct contact with the liquid such as the gas-permeable membranes of electrochemical gas sensors. In the case of optical measuring methods, for example, in the case of a haemoglobin determination, the part of the sensory element which contains the liquid volume to be analysed at the time of determination of the measured value can also be regarded as a fluidic component. Fluidic components are often made of materials which are adapted to the requirements of the fluidic components. Thus, for example, tubes are often made of silicone rubber or soft polyvinyl chlorides, pipes can be made of polyvinyl chlorides, polyamides or acrylonitrile-butadiene copolymers, channel systems can be made of polycarbonates, polymethylmeth-acrylates, acrylonitrile-butadiene copolymers or styrene-methmethacrylic-butadiene copolymers, connectors can be made of polypropylenes, polycarbonates or polyamides, dock elastomers can be made of nitrile rubbers, silicone rubbers or fluorinated rubbers, filling mouths can be made of silicone rubbers or polyether ether ketones, bottles and liquid containers can be made of polyethylenes, and sealing elements can be made of natural rubbers, silicone rubbers or fluorinated rubbers, inter alia.

A fluidic system in the sense of the present application can be regarded as a combination of several fluidic components which are connected together in such a manner that liquid can be transported between these fluidic components. In particular, such fluidic systems are suitable for taking up, conveying or dispensing liquids. By combining various fluidic components to form a fluidic system it is possible to combine the functions of individual fluidic components such that the resulting fluidic system can also perform complex fluidic functions. Thus, for example, a fluidic system that can transport defined liquid volumes over a defined path can be generated by a suitable combination of tubes, valves and pumps. Such fluidic systems can contain any number of fluidic components and can be of any degree of complexity. A single component which can undertake functions of several fluidic components due to its spatial structure can also be regarded as a fluidic system. Such complex components can for example be manufactured in an injection moulding process which allows especially complex channel systems to be manufactured in a single component. Fluidic systems are used in particular in analytical systems where the liquid-conveying areas of sensory elements are also regarded as a component of the fluidic system.

In accordance with at least one embodiment of the present invention, an analytical system is regarded as any system which has at least one sensory element for determining at least one physical or chemical parameter of a liquid and a fluidic system for transporting liquids to or from the sensory element. Analytical systems can have several fluidic partial systems that are independent of one another or connected to one another as well as several sensory units or modules. For example, an analytical system can have a fluidic partial system for transporting sample or quality control liquids and a fluidic partial system for transporting liquid or also gaseous calibration media and/or washing or cleaning media which are, for example, connected by valves to form a total fluidic system.

In the sense of the present application sensory elements can be regarded as all devices that can be used to determine physical or chemical parameters of a liquid. These can be in particular sensors which come into direct contact with the sample to be examined or sensory systems which indirectly determine the physical or chemical parameters for example by means of optical measurements of transmission or scattered light. Sensors of the former type can for example be electrochemical or optical sensors for determining the gas values, the pH value, the ion values or the metabolite values of blood samples. Sensory systems of the second type can for example be optical measuring devices for determining haemoglobin values of blood samples. Sensors of the former type come into direct contact with the liquid to be examined such that the liquid-conveying area of such sensory elements functions as a fluidic component. In sensory systems of the second type the area of the system which is used to transport liquid and in particular the area of the system which contains the liquid volume to be analysed at the time of determining the measured value can be functionally regarded as a fluidic component. For example, they can be spectroscopic measuring paths within the fluidic system or cuvettes in the case of optical measuring systems.

In accordance with at least one embodiment of the present invention, a sensory module is generally regarded as a combination of several sensory elements. Such sensory modules can in particular have several sensory elements within a common housing which has a common fluidic partial system. Such sensory modules can for example be designed as cassettes or sensory arrays that can be used to substantially simultaneously determine a plurality of physical or chemical parameters on the basis of a single sample. Such sensory modules can for example nave a fluidic system with a single fluidic inlet, an open or branched fluidic transport space comprising one or more channels and a single fluidic outlet. Several sensory elements can be in contact with the common fluidic transport space which thus functions as a common sample channel within this sensory module.

In the sense of the present application inner surfaces of a fluidic component or of a fluidic system can be regarded as the surfaces which come into contact with the liquid to be transported in the spatial form in which the fluidic component is used for liquid transport. These are for example the inner walls of tubes, pipes or channels that can be in contact with a liquid that flows through them. However, in this connection the entire inner surface of the fluidic component does not necessarily have to come into contact with the liquid.

Hydrophilic polymers are understood in the sense of the present application as polymeric substances which are composed of monomer building blocks of the same type or different types and have hydrophilic properties. The polymer chains of such polymers are hydrophilic or at least have hydrophilic chain sequences. Such hydrophilic polymers have chemical groups with a high affinity for water such as hydroxyl or ether groups. Examples of hydrophilic polymers are certain polyethers such as certain polyethylene glycols or certain polypropylene glycols, certain polysaccharides such as certain dextrans or certain polyalcohols such as certain polyvinyl alcohols. In particular, certain polyether-polyurethane copolymers can also be used as hydrophilic polymers. In accordance with the present invention, the hydrophilic polymer does not have to be produced only on the coated surface but rather the hydrophilic polymer chains can already be applied to the surface in the form of a solution. This distinguishes the present invention especially from hydrophilic coatings which are produced by polymerizing precursors, especially by means of plasma polymerization or graft polymerization, on a surface since the process according to the invention which uses already polymerized hydrophilic polymers that are essentially composed of non-covalently cross-linked polymer chains does not require complicated polymerization steps. Another disadvantage of coating processes by means of polymerization from precursors on a surface is that the reproducibility of manufacturing thin layers depends on many factors and can thus not always be ensured. The use of such hydrophilic polymers according to the present invention enables a hydrophilic coating to be produced directly and simply without additional chemical reaction steps. For this purpose the polymer chains do not necessarily have to be cross-linked with one another in order to achieve a durable hydrophilic coating. By using polymers according to the present invention they can arrange to form a durable film of a hydrophilic polymer even without covalent cross-linkages. Hence, hydrophilic polymers can be typically used which are composed of non-covalently cross-linked polymer chains. The use of hydrophilic polymers that are already polymerized is less time-consuming than the polymerization of precursors on the surface of a substrate to form a thin film.

Hydrophilic polymers in the sense of the present application are in particular polymer molecules that are already polymerized, in particular longer-chained polymer molecules which are not covalently cross-linked together and thus can still be dissolved in adequate amounts in suitable solvents. In this case non-covalently cross-linked is understood to mean that the individual polymer chains are essentially not covalently linked together. However, it is basically possible that unspecific covalent bonds can subsequently form to a slight extent between individual polymer chains and/or individual polymer chains and the surface after the non-covalently cross-linked polymer chains according to the invention have been applied to the surface to be coated and formation of the polymer film or form as a result of subsequent processes e.g., during storage. Such bonds that may for example form unspecifically as a result of plasma treatment between the individual polymer chains or between the polymer chains and surface are, however, not essential for the production and/or the inventive properties of the polymer film. They can therefore be clearly differentiated from the chemical bonds between individual molecules and/or a surface in the case of polymer films that are only produced on the surface to be coated from precursors for which these chemical bonds that are formed are essential and decisive for the production and properties of the polymer film that is formed.

A film in the sense of the present application is understood as a substantially continuous and uniform layer of a substance on a substrate which is produced in particular by applying the substance to be applied in a dissolved form on the surface to be coated whereby the film is formed by removing the solvent or solvent mixture.

The term surface wettability or wettability is used in the sense of the present application as a measure for the hydrophilic or hydrophobic properties of a surface. Surfaces and substances that can be readily wetted by aqueous liquids generally have a high hydrophilicity. The wetting angle or contact angle is specified as a measure of wettability which is understood as the angle which a tangent to the contour of the drop makes relative to the surface of the solid body in the three phase point and which represents a measure for the wettability of a surface or interface by another phase. The smaller the wetting angle, the higher is the wettability and the more hydrophilic is the surface. A surface can be wetted by water especially when the wetting angle is less than 90°.

All substances and substance mixtures that are liquid under normal conditions and have a water content of more than 50% by weight are regarded as aqueous liquids or solutions in the sense of the present application. They may be solutions or homogeneous or heterogeneous mixtures such as dispersions, emulsions or suspensions. In particular, they can be sample liquids in particular body fluids or fluids derived therefrom such as blood, plasma, serum, urine, cerebrospinal fluid, tear fluid, dialysate or such like. The aqueous liquids can also be salt solutions, buffer solutions, calibration solutions, reference solutions, quality control solutions, washing or cleaning solutions, reagent solutions or solutions containing standardized analyte concentrations, so-called standards.

In the sense of the present application, organic solvents and solvent mixtures are solvents and solvent mixtures having a water content of less than 50% by weight.

The processes and devices according to the present invention enable a fluidic system to be provided which allows the wetting properties of the inner surfaces of the individual fluidic components to be matched to one another. This can reduce the risk of gas bubbles attaching or forming on the inner surfaces of the fluidic system during a long period of use. This is achieved according to the present invention by the presence of a thin film of the same hydrophilic polymer on the inner surfaces of the fluidic components or of the fluidic system. Such thin films of a hydrophilic polymer on the inner surfaces of fluidic components can be particularly simply and economically produced by the process according to the present invention. Furthermore, the films of hydrophilic polymer produced by the process according to the present invention adhere strongly to the inner surfaces of the fluidic components and are very resistant to physical or chemical stress so that they are especially suitable for use in diagnostic analyzers.

The process according to an embodiment of the present invention can be characterized by the following sequence of steps:

1. Firstly the inner surfaces of the fluidic component are subjected to a physicochemical treatment (pre-treatment).

In this process at least the part of the inner surfaces of the fluidic component is treated which is subsequently provided with the film of the hydrophilic polymer. For this it is not absolutely necessary that during this treatment the component is present in the form in which it is later present as a fluidic component in a fluidic system. In certain embodiments and especially in the case of flexible or elastic components, the accessibility of the inner surfaces to this treatment can be increased by changing the shape of the component before treatment. Thus, for example, pieces of tubing can be subjected to a treatment of their inner surface by firstly turning the piece of tubing inside out such that the inner surface is now facing outwards, subsequently this surface which is now facing outwards is treated and finally the piece of tubing is again turned in such that the pretreated surface is now again facing inwards. In another embodiment the outer side of a piece of tubing can be firstly subjected to the treatment. Subsequently the piece of tubing is turned inside out such that the treated surface of the piece of tubing becomes its inner surface. In other embodiments it is possible that firstly the surfaces of individual elements of the fluidic component are subjected to the treatment and these elements are subsequently assembled to form the fluidic component. This can be especially advantageous when, in a complex fluidic component the inner surfaces are not or not readily accessible to such a treatment. A pre-treatment of the inner surfaces improves particularly the adhesion of the film of the hydrophilic polymer to the inner surfaces and the resistance of the applied film to physical or chemical stress. Physical stress can in particular be understood as repeated contact over a long time with aqueous sample liquids and in particular with body fluids such as blood, plasma, serum or urine. Such physical stress over a long time period can reduce the layer thickness of the film of hydrophilic polymer in the course of time or the film may wholly or partially detach from the inner surfaces of the fluidic component. Chemical stresses can among others be contact with aggressive chemical reagents such as aggressive cleaning solutions. Treatment of the inner surfaces before applying the film of hydrophilic polymer can be carried out with physicochemical methods, typically by means of a plasma treatment. However, it is basically possible to use other physicochemical methods to pretreat the membrane such as ion beam treatment or treatment with an oxidizing substance such as a sodium naphthalene solution. Such methods for surface treatment are known and described for example in "Surface Modification of Poly(tetrafluoroethylene) Film by Chemical Etching, Plasma and Ion Beam Treatments", Kim S., Journal of Applied Polymer Science, 2000, vol. 77, p. 1913-1920 or in WO 94/06485 (Chatelier et al.). Chemical methods for surface treatment are typically not those methods in which additional intermediate layers such as adhesion agent layers are applied. Rather, in accordance with the present application, those methods are regarded as typical physicochemical methods for surface treatment which result in an increase in the reactivity of the surfaces without substantially changing the chemical composition of the surfaces. In a typical embodiment, the inner surfaces of the fluidic component are treated by plasma treatment before producing the film of the hydrophilic polymer. Treatment of the inner surfaces with a plasma before applying the polymer solution achieves a bond between the inner surfaces and the polymer film that adheres sufficiently well as a high resistance of the film to physical or chemical stress. Such a physical plasma treatment allows one to dispense with the use of toxic chemicals for surface treatment. A pre-treatment of the inner surfaces with a gas plasma results in a homogeneous modification of the surface which extends only into low depths of the surface material. In such plasma methods for surface pretreatment a gas plasma containing ionized particles is generated by electrical discharge or by beaming electromagnetic fields into a gas atmosphere under reduced pressure. This gas plasma can be used to generate reactive areas on the surfaces and thus at least to temporarily increase its reactivity such that the adhesion of the polymer film to the inner surfaces and its resistance to physical or chemical stress can be increased.

2. In a next process step the inner surfaces of the fluidic component are contacted with a solution of the hydrophilic polymer.

This contacting the inner surfaces of the fluidic component with the solution of the hydrophilic polymer can be provided by all methods known to a person skilled in the art such as, for example, rinsing or filling the fluidic component with the solution, immersing the fluidic component in the solution, or spraying the solution on the inner surfaces. In this process it is possible to provide the entire inner surface of the fluidic component with a film of the hydrophilic polymer or only certain partial areas of the inner surfaces. In particular, these partial areas can be those that later come into contact with liquids in a fluidic system. In a typical embodiment, a solution of a hydrophilic polymer is used in this process step which is soluble in organic solvents or solvent mixtures and/or is substantially insoluble in aqueous solutions and, in particular, in the sample liquids and aqueous cleaning or calibration solutions. In particular, the use of such hydrophilic polymers enables the inner surfaces of the fluidic components to be permanently and durably coated in an efficient manner without additional chemical reaction steps. The use of hydrophilic polymers that are substantially insoluble in aqueous solutions can substantially reduce dissolution of the film in aqueous liquids and hence such films are very durable in such media and are thus especially suitable for use in diagnostic analytical systems. In a typical embodiment, a polyether-polyurethane copolymer is used as a hydrophilic polymer. Such polyether-polyurethane copolymers are described for example in the following U.S. patents: U.S. Pat. Nos. 5,728,762 and 5,932,200 to Reich et al. Such typical polyether-polyurethane copolymers are block copolymers with hydrophilic regions and hydrophobic regions. As a result of these amphiphilic properties the polymers dissolve well in certain organic solvents and solvent mixtures, on the other hand they organize themselves after removal of the organic solvent or solvent mixture to form hydrogels with hydrophilic surface properties that are substantially insoluble in aqueous solutions and are thus particularly suitable for a coating according to the present invention. Such particularly suitable polyether-polyurethane copolymers can for example be obtained from CardioTech International, Inc., Woburn, Mass., USA.

In accordance with one embodiment of the instant invention, the film can be produced by making the film of the hydrophilic polymer directly on the inner surfaces of the fluidic component without further intermediate layers. As a result of the surface treatment according to the invention this surface is modified in the first process step in such a manner that there is an adequate adhesion bond between the inner surfaces and the polymer film as well as a high resistance of the film to physical or chemical stress. As a result complicated application of additional intermediate layers such as bonding agent layers on the surface is not necessary before applying the film of the hydrophilic polymer.

3. In a next process step the solution of the hydrophilic polymer is replaced by a gaseous medium in such a manner that firstly the inner surfaces of the fluidic component remain wetted with a part of the solution of the hydrophilic polymer.

In this process any excess of polymer solution that may be present is removed by the introduction of a gas volume such that a certain amount of polymer solution remains on the surface to be coated. The excess polymer solution can be removed actively or passively. In particular, this can be carried out by introducing the gaseous medium in such a manner that the fluidic component is flushed with this gaseous medium and thus the excess polymer solution is displaced by this medium. In other embodiments this can be achieved by removing the fluidic component from the solution of hydrophilic polymer and allowing excess polymer solution to drain off the surfaces of the fluidic component to be coated and replacing it by the surrounding gaseous medium, in particular, air. Furthermore, it is possible to specifically define and adjust the thickness of the film of hydrophilic polymer applied to the surface by adjusting the amount and/or concentration of the polymer solution remaining on the surface.

4. In a final process step, a film of the hydrophilic polymer is produced on the inner surfaces of the fluidic component by removing the solvent or solvent mixture.

In this final process step, the solvent or solvent mixture of the polymer solution remaining on the surfaces is removed such that finally a film of the hydrophilic polymer remains on this surface. This removal of the solvent or solvent mixture is carried out at least to such an extent that a mechanically stable film of the hydrophilic polymer remains on the surface. The solvent or solvent mixture can in this case be removed passively for example by slow evaporation in the outer atmosphere or be actively accelerated for example by applying a vacuum or underpressure, by flushing the surface with a gas, or by accelerating evaporation by increasing the temperature.

In certain embodiments of the process it is possible to firstly provide surfaces of individual components or areas of the fluidic component and especially liquid-conveying areas thereof with a film of the hydrophilic polymer and to subsequently assemble these elements to form the fluidic component.

Another aspect of the present invention concerns fluidic components which are characterized in that a film of a hydrophilic polymer is present directly on the inner surfaces of the fluidic components without other intermediate layers. In particular, the present invention concerns fluidic components with a film of a hydrophilic polymer on their inner surfaces wherein the film of hydrophilic polymer has been produced by one of the processes according to the invention described above.

The presence of a film of a hydrophilic polymer on the inner surfaces modifies the physical surface properties of the fluidic component. In particular, such a coating can increase the ability of these surfaces to be wetted with aqueous solutions and thus reduce the risk of gas bubble inclusions or formation. Another effect of the presence of such a polymer film on the inner surfaces of fluidic components is that any existing unevenness of these surfaces in the nano- to micrometer range can be largely compensated by producing the film on these surfaces. This is especially advantageous when such fluidic components are used in diagnostic analytical systems since such analytical systems often have an increased risk of contamination due to substances remaining from previous measurements or cleaning steps. Such substances, in particular cellular or macromolecular substances from body fluids such as proteins, preferably deposit on rough or very inaccessible surface areas. The presence according to the invention of a stable film of a hydrophilic polymer on these surfaces reduces the risk of such contamination over a long period of use.

In a typical embodiment, the inner surfaces of the fluidic component consist of a plastic. Plastics in the sense of the present application and also according to a definition of the Standards Commission for "Plastics in the DIN" are understood as "materials whose essential components are composed of macromolecular organic compounds which are formed synthetically or by modification of natural products". In many cases they can be melted and moulded under certain conditions such as heat or pressure. The properties of rubbers and chemical fibres also includes them among the plastics. Plastics are especially suitable as materials for fluidic elements since their properties can be modified in a wide variety of ways and can thus be optimally adapted to the functions that have to be fulfilled in fluidic systems, for example by modifying their elasticity. Many plastics can be moulded in various processes known to a person skilled in the art such as injection moulding or deep drawing processes such that as a result the shape of fluidic components can be specifically adapted to their function in the fluidic system. The following plastics are used among others as materials for fluidic components: polyamides, polycarbonates, polypropylenes, polyethylenes, polymethylmethacrylates, polyvinyl chlorides, polyether ether ketones, acrylonitrile-butadiene copolymers, styrene methmeth-acrylic-butadiene copolymers, natural rubbers, silicone rubbers, nitrile rubbers or fluorinated rubbers.

In a typical embodiment, the thickness of the film of hydrophilic polymer on the inner surfaces of these components is between about 0.01 and about 50 µm, typically between about 0.01 and about 10 µm, more typically between about 0.01 and about 5 µm. The application of thin polymer films on the inner surface of fluidic components enables, on the one hand, the requirements with regard to the surface properties of the fluidic components and in particular their wettability or surface structure to be fulfilled and, on the other hand, the production of such thin films enables a particularly cost-saving and thus economical use of the hydrophilic polymer.

Another aspect of the present invention concerns fluidic systems for transporting liquids which consist of several fluidic components which are connected in such a manner that liquids can be transported between these fluidic components and comprise at least one fluidic component according to the invention. In fluidic systems consisting of several fluidic components, gas bubbles can form or become attached or contaminating substances may be deposited especially at sites of contact of the individual fluidic components at which there is a sudden transition in the wetting properties of the inner surfaces of the various fluidic components, for example due to different surface materials. According to the present invention, this problem can be solved by the presence of a film of a hydrophilic polymer, typically of the same hydrophilic polymer, on the adjoining inner surfaces of the individual fluidic components. The presence of a film of the same hydrophilic polymer on the inner surfaces of the individual fluidic components matches the physical properties of these components and in particular their wetting properties and, thus, substantially prevents contamination.

According to the present invention, a film of a hydrophilic polymer does not have to be present over the entire inner surfaces of the fluidic system. In many cases it is sufficient when such a film is only present in certain areas of the fluidic system or on the inner surfaces or parts of these surfaces of certain fluidic components. If fluidic systems are used in analytical systems and in particular in diagnostic analytical systems, it is often sufficient for an accurate and error-free determination of the measured values to provide those areas of the fluidic system with a film of a hydrophilic polymer which, beginning at the sample application device are on the transport path upstream of the respective sensory element or in the liquid-conveying area of the sensory element itself. Other areas of the fluidic system that should be typically provided with a film of a hydrophilic polymer are the areas which are located in the fluidic system also upstream of the sensory elements but do not transport sample liquid but, rather, for example, transport calibration or cleaning media and often flow into the transport path of the sample liquid upstream of the sensory elements. The areas of the fluidic system that are downstream of the sensory element, such as the transport lines to the waste containers, do not necessarily have to have a film of the hydrophilic polymer since gas bubbles or contamination of these areas do not have adverse effects on the determination of measured values.

Another aspect of the present invention concerns processes for producing such fluidic systems which have a film of a hydrophilic polymer at least partly on their inner surfaces.

In a typical embodiment, such a fluidic system is produced by producing the film of a hydrophilic polymer firstly on the inner surfaces of individual fluidic components or in smaller subassemblies of such fluidic components that are subsequently assembled to form the fluidic system. This process can be used especially in cases in which it is not economically appropriate to coat the entire fluidic systems or large parts thereof or when it is technically impossible or very difficult for example due to the fact that individual subareas of the system are not accessible or not readily accessible to such a coating. These may for example be subareas of the fluidic system behind valves or very narrow liquid transport paths. However, in order to nevertheless produce a film of a hydrophilic polymer in such areas of the fluidic system, the individual fluidic components whose inner surfaces should be provided with a film of a hydrophilic polymer are firstly individually provided with such a film and subsequently assembled to form a fluidic system. In this manner it is possible to also provide parts of the system with a film of a hydrophilic polymer in a simple manner which would not be accessible to such a coating or would be very difficult to access in the assembled system.

In another typical embodiment, such a fluidic system is produced by firstly physicochemically pretreating the inner surfaces of the individual fluidic components, subsequently assembling these components to form a fluidic system and to carry out the other process steps according to the invention on this assembled fluidic system. This procedure can be used especially in cases in which a physicochemical pre-treatment of the entire fluidic system or large parts thereof is not economically viable or is impossible or very difficult for technical reasons, for example, due to the fact that individual subsections of the system are not accessible or difficult to access for such a pretreatment. In some pre-treatment methods and especially in the case of a plasma treatment the problem sometimes occurs that the effect of the pretreatment is restricted to readily accessible areas of the fluidic system, whereas areas of the fluidic system that are difficult to access cannot be pre-treated or are very difficult to pretreat. In order to overcome this problem a process is herewith provided which solves this problem by not subjecting the entire fluidic system or large parts thereof to such a pre-treatment, but rather to firstly only use the pretreatment for individual fluidic components or parts thereof which can thus be more easily be pretreated. Thus, for example, the individual elements of a valve or segments of a long piece of tubing can be individually pretreated and subsequently assembled. The other steps for producing the film of a hydrophilic polymer on the inner surfaces of the fluidic system are often no longer critical and can be carried out in the assembled system.

In the aforementioned embodiments the film can also be produced by carrying out the process steps described for the individual fluidic components on smaller subassemblies of several such fluidic components. For example, fluidic components such as a tube or an elbow can be assembled as small subassemblies before the start of the process according to the invention and be subjected as a common small subassembly to the subsequent steps for producing a film of a hydrophilic polymer on the inner surfaces.

Another aspect of the present invention concerns analytical systems for determining at least one physical or chemical parameter of a liquid which comprises at least one sensory element for determining at least one physical or chemical parameter of the liquid and a fluidic system according to the invention to transport liquids to the sensory element and/or from the sensory element.

In such an analytical system it is possible to use all previously described embodiments of fluidic systems according to the invention. Such analytical systems can in principle be used to analyse all types of liquids and in particular to analyse aqueous liquids. In a typical embodiment, such analytical systems are used to analyse physiological liquids such as blood, plasma, serum, urine, cerebrospinal liquid, tear fluid or liquid biological samples such as cell suspensions, cell supernatants, cell extracts, tissue lysates or such like. They are more typically used to analyse blood, serum, plasma or urine.

In a typical embodiment, a film of the hydrophilic polymer is also present on the inner surfaces of the liquid-conveying areas or one or more sensory elements of the analytical system. These liquid-conveying areas of sensory elements are in direct contact with the liquid to be analysed. The presence of a film of a hydrophilic polymer in these areas is particularly advantageous since it can reduce the risk of falsification of measured values by the presence of gas bubbles or contaminating substances in the sensory element. In other typical embodiments, such a risk can be further reduced by the presence of a film of the same hydrophilic polymer on the liquid-conveying areas of the sensory element as well as on the adjoining parts of the remaining fluidic system.

In still another typical embodiment, the analytical system comprises several sensory elements to determine different physical and/or chemical parameters of a liquid which are usually used for many determinations. In addition to sensory elements that can be used repeatedly and many times, it is, however, also possible to use sensory elements that can only be used once. The various elements in this case are usually connected together by fluidic components that can also be in direct contact with one another. Various sensory elements can also in this connection be combined into sensory modules which have a common fluidic partial system.

In order that the invention may be more readily understood, reference is made to the following examples, which are intended to illustrate the invention, but not limit the scope thereof.

EXAMPLES

Example 1

A System for Determining Several Diagnostically Relevant Parameters from Sample Liquids Using a Complex Fluidic System An example of a system for determining several diagnostically relevant parameters from sample liquids using a complex fluidic system is the Omni S analytical system from Roche Diagnostics GmbH. The parameter profile of this system that is arranged in modules encompasses blood gases, electrolytes, total haemoglobin, CO oximetry, metabolites and bilirubin and it requires only small sample volumes and is hence particularly suitable for use on neonatal wards.

FIG. 1 shows a schematic overview of the fluidic system of the Omni S system. In this case the connecting lines between the individual fluidic components represent fluidic connections which can be designed as tubes or pipes depending on the intended use. The small circles shown within these fluidic connections represent valves that can be used to control the liquid transport. They are typically designed as pinch valves. Bars that are vertical to the fluidic connections represent coupling elements that can be used to bring the fluidic subassemblies into contact with one another. The fluidic connections drawn as triple lines represent the sample path of a liquid sample from the filling mouth (8) to the sensory modules (1a) to (1d). Each of the areas (1a) to (1d) symbolizes sensory modules which can consist of several sensory elements. Thus, the sensory module (1a) can contain elements for determining metabolites such as lactate, urea or glucose, the sensory module (1b) can contain ion-selective electrodes for determining calcium, potassium, sodium or chloride, the sensory module (1c) can contain blood gas sensors for determining the partial pressure of oxygen and carbon dioxide as well as for determining the pH value and the sensory module (1*d*) can contain sensory elements for determining haemoglobin and haemoglobin derivatives. The sample to be examined is introduced into the fluidic system of the analytical system via the filling mouth (8) from where it is transported along the sample path to the various sensory modules (1*a*) to (1*d*), whereby the sample is additionally aliquoted during the transport. This function is undertaken by the valves located in the sample path. Liquids for quality control purposes can also be introduced through the filling mouth and be transported on the same sample path as the samples themselves to the sensory modules. The course of liquid transport along the sample path is monitored by the physical sample sensors (7) which among others give information on the filling level of the system. The introduced sample is divided among the sensory modules (1*a*) to (1*c*) within the channel system (2) in which valves are again integrated. Liquids for cleaning or calibration purposes are present in the liquid containers (6) which are connected to the remaining fluidic system by tubes or pipes and can be fed into it in a controlled manner by means of valves. These solutions and also the sample solutions are transported by means of the peristaltic pumps (3) which are connected to the fluidic system via valves. Consumed samples and liquids are transported by means of a vacuum pump (5) via the fluidic system from the sensory modules to a collecting container (9) which ends in a waste container (4).

Example 2

Figure 2:
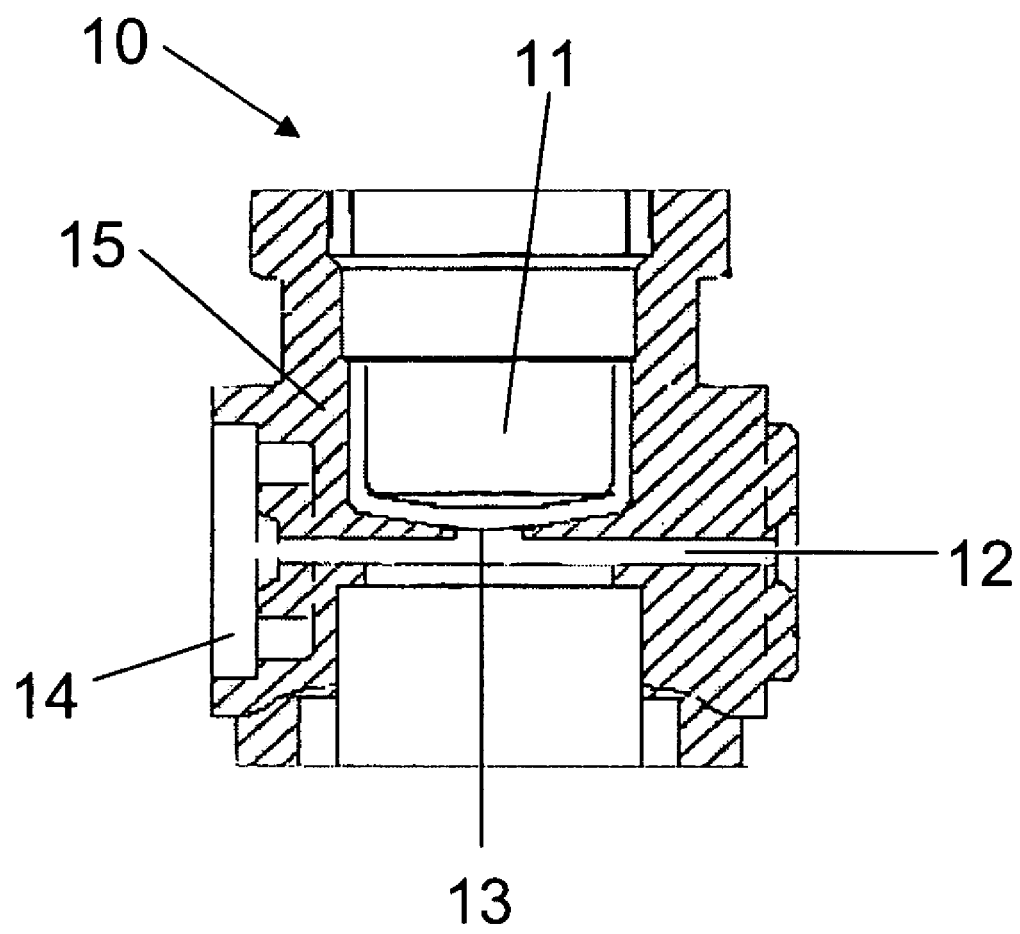
FIG. 2 is a partial, cross-sectional view through the sensory area of a sensor element of an analytical system in accordance with one embodiment of the present invention.

Preparing a Film of a Hydrophilic Polymer on a Fluidic Element Pretreated with Plasma Using a Housing Channel as an Example The housing channel of a sensory element, for example an oxygen electrode, is described in the following as an example of a fluidic component. Such housing channels essentially correspond to liquid-conveying areas of sensory elements which are in direct contact with liquids and in particular include the sample channel that supplies and removes liquids within the sensory element. FIG. 2 shows an example of a section through the sensory area of such a sensor element using an oxygen sensor of the Clark type as an example that is used for example in the OMNI analytical system from Roche Diagnostics. These sensory elements (10) include a sample or housing channel (12) to transport and provide the sample in addition to the actual sensor (11) having an inner electrolyte space and electrodes located therein. A gas-permeable and substantially ion- and liquid-impermeable plastic membrane (13) which separates the inner electrolyte space and sample channel is located between the inner electrolyte space and sample channel. In the case shown the housing of the sensory element (15) and thus also the walls of the housing channel (12) consist of a transparent plastic for example a methylmethacrylate-butadiene-styrene copolymer. In order to pretreat the housing channel before the actual hydrogel coating, the housing (15) is fixed on a support plate and placed in a plasma apparatus of the type V 15-G from the Plasma-finish Company and treated with a helium plasma according to the manufacturer's instructions for a few minutes at 2.45 GHz. In the case shown the plasma can reach the inner sides of the housing channel through the openings on both sides of the housing channel (12) as well as through the opening in the housing which is later covered by the membrane (13). Within ca. 5-60 minutes after completion of the plasma treatment, the plasma-treated housing is removed from the support plate and fixed in a housing support. In this housing support the liquid lines supplying and discharging liquids are now attached to both ends of the housing channel (12). The liquid lines are sealed by press connections via the compressible seals (14) present on the housing (15) or a seal present on the liquid line. A solution of hydrophilic polymer X1 is sucked for a few minutes through the liquid lines and hence through the housing channel (12). X1 represents a hydrophilic polymer of the polyether-polyurethane copolymer type which can for example be obtained as "hydrophilic polyether polyurethane" from CardioTech International, 78 E Olympia Avenue, Woburn Mass. 01801-2057, USA and has a water uptake rate of 50% and an expansion rate by swelling of 60%. In order to prepare a solution of hydrophilic polymer X1, a defined amount of the hydrogel granulate X1 is dissolved in an ethanol-water mixture while stirring. Subsequently, the solution of hydrophilic polymer X1 is removed from the liquid lines and the housing channel (12) and air is sucked for a few minutes through the liquid lines and the housing channel. The hydrogel layer is dried in this process on the inner walls of the housing channel (12) so that the result of the coating process according to the invention is a film of the hydrophilic polymer on the inner walls of the housing channel (12).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it in contemplated that the present invention is not necessarily limited to these preferred aspects of the invention.

What is claimed is:

1. A fluidic system for transporting liquids comprising two or more fluidic components assembled so as to be in fluid communication, each of said fluidic components having at least one fluid-conveying surface, wherein a film of the same hydrophilic polymer is present on each fluid-conveying surface of each fluidic component, said film having a surface wettability greater than the wettability of at least one of said fluid-conveying surfaces of said fluidic components in the absence of said film, and wherein at least one of said fluidic components has a fluid-conveying surface that adjoins a fluid-conveying surface of another of said fluidic components, each of said adjoining fluid-conveying surfaces of said two fluidic components being provided with a continuous film of the same hydrophilic polymer.

2. An analytical system for determining at least one physical or chemical parameter of a liquid, said system comprising at least one sensory element for determining at least one physical or chemical parameter of the liquid, and at least one fluidic component for transporting liquids to the sensory element and/or from the sensory element, wherein said at least one sensory element has a fluid-conveying surface that adjoins a fluid-conveying surface of said at least one fluidic component, wherein a continuous film of the same hydrophilic polymer is present on each of said adjoining fluid-conveying surfaces, said film having a surface wettability greater than the wettability of at least one of said fluid-conveying surfaces in the absence of said film, and wherein said fluid conveying surface of said at least one sensory element comes into direct contact with the sample to be examined.

3. The analytical system of claim 2, wherein the liquid to be analysed is a physiological liquid.

4. The analytical system of claim 3, wherein the physiological liquid is selected from blood, serum, plasma, urine, or combinations thereof.

5. The analytical system of claim 2 wherein the analytical system contains a plurality of sensory elements.

6. The analytical system of claim 5, wherein the plurality of sensory elements are combined within at least one sensory module, and wherein the sensory module is characterized to determine various physical and/or chemical parameters of a liquid.

7. The analytical system of claim 2, wherein the fluidic component is a channel, tube, pipe, valve, distributor, coupling element, liquid receiving device, nipple, or liquid-conveying area of a sensory element or liquid container.

8. The analytical system of claim 2, wherein the film of the hydrophilic polymer has a thickness of between about 0.01 and about 50 µm.

9. The analytical system of claim 8, wherein said thickness is between about 0.01 and about 10 µm.

10. The analytical system of claim 8, wherein said thickness is between about 0.01 and about 5 µm.

11. The analytical system of claim 2, wherein the hydrophilic polymer is a block copolymer with hydrophilic regions and hydrophobic regions.

12. The analytical system of claim 2, wherein the hydrophilic polymer is a polyether-polyurethane copolymer.

13. A process for the production of a fluidic system of claim 1, wherein said two or more fluidic components are assembled to form the fluidic system; and the process steps i) to iii) hereafter, are carried out on the assembled fluidic system:
 i) the liquid conveying surfaces of the assembled fluidic system are brought into contact with a solution of the hydrophilic polymer,
 ii) the solution of the hydrophilic polymer is replaced by a gaseous medium in such a manner that first the liquid conveying surfaces of the assembled fluidic system remain wetted with part of the solution of the hydrophilic polymer, and
 iii) a film of the hydrophilic polymer remains on the liquid conveying surfaces of the assembled fluidic system by removing the solvent,
and wherein at least one of said assembled fluidic components has a fluid-conveying surface that adjoins a fluid-conveying surface of another of said assembled fluidic components, said adjoining fluid-conveying surfaces of said two assembled fluidic components being provided with a continuous film of the same hydrophilic polymer.

14. A sensory module system for determination of at least one physical and/or chemical parameter of a liquid sample, said sensory module system comprising a plurality of sensory elements and a fluidic partial system for transporting liquid to and/or from a sensory element wherein a film of the same hydrophilic polymer is present both on liquid conveying surfaces of at least one said sensory element and on each liquid conveying surface of the said fluidic partial system, and wherein said film consists essentially of polymer molecules that are not covalently cross-linked, and wherein said at least one sensory element has a fluid-conveying surface that adjoins a fluid-conveying surface of said fluidic partial system, said adjoining fluid-conveying surfaces of said at least one sensory element and said fluidic partial system being provided with a continuous film of the same hydrophilic polymer.

15. The sensory module system of claim 14, wherein said module system comprises one or more cassettes or sensory arrays, each such cassette or array comprising a plurality of sensory elements to determine substantially simultaneously a plurality of physical or chemical parameters of a single sample.

16. The sensory module system of claim 14, wherein said fluidic partial system comprises a single fluidic inlet, an open or branched fluidic transport space comprising at least one channel, and a single fluidic outlet.

17. The fluidic system of claim 1 wherein said fluidic components are selected from the group consisting of a channel, tube, pipe, valve, distributor, coupling element, liquid receiving device, nipple, liquid-conveying area of a sensory element or liquid container.

18. The fluidic system of claim 1, wherein the film of the hydrophilic polymer has a thickness of between about 0.01 and about 50 µm.

19. The fluidic system of claim 18, wherein said thickness is between about 0.01 and about 10 µm.

20. The fluidic system of claim 19, wherein said thickness is between about 0.01 and about 5 µm.

21. The fluidic system of claim 1 wherein the hydrophilic polymer is a block copolymer with hydrophilic regions and hydrophobic regions.

22. The fluidic system of claim 21 wherein the hydrophilic polymer is a polyether-polyurethane copolymer.

* * * * *

UNITED STATES PATENT AND TRADEMARK OFFICE
CERTIFICATE OF CORRECTION

| | | |
|---|---|---|
| PATENT NO. | : 8,394,338 B2 | Page 1 of 1 |
| APPLICATION NO. | : 11/106143 | |
| DATED | : March 12, 2013 | |
| INVENTOR(S) | : Weis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 997 days.

Signed and Sealed this
Sixteenth Day of December, 2014

Michelle K. Lee
*Deputy Director of the United States Patent and Trademark Office*